(12) United States Patent
Mitra et al.

(10) Patent No.: US 8,478,541 B2
(45) Date of Patent: Jul. 2, 2013

(54) EXTRACTING GENE-GENE INTERACTIONS FROM GENE EXPRESSION DATA

(75) Inventors: Sushmita Mitra, Kolkata (IN); Chivukula Anjaneya Murthy, Kolkata (IN); Ranajit Das, Kolkata (IN)

(73) Assignee: Indian Statistical Institute, Kolkata (IN)

( * ) Notice: Subject to any disclaimer, the term of this patent is extended or adjusted under 35 U.S.C. 154(b) by 465 days.

(21) Appl. No.: 12/854,116

(22) Filed: Aug. 10, 2010

(65) Prior Publication Data

US 2012/0041912 A1 Feb. 16, 2012

(51) Int. Cl.
*G01N 33/50* (2006.01)

(52) U.S. Cl.
USPC ............................................................. 702/19

(58) Field of Classification Search
None
See application file for complete search history.

(56) References Cited

U.S. PATENT DOCUMENTS

2008/0027954 A1  1/2008  Gan et al.

OTHER PUBLICATIONS

Androulakis, I.P., et al., "Analysis of Time-Series Gene Expression Data: Methods, Challenges, and Opportunities," Annual Review of Biomedical Engineering, vol. 9, pp. 205-228, 2007.
Turner, H., et al., "Improved Biclustering of Microarray Data Demonstrated Through Systematic Performance Tests," Computational Statistics & Data Analysis, vol. 48, Issue 2, pp. 235-254, Elsevier, Amsterdam, 2005.
http://db.yeastgenome.org/cgi-bin/GO/goTermFinder, accessed on May 3, 2010, pp. 1-1.
http://www.yeastgenome.org, accessed on May 3, 2010, pp. 1-3.
Kim, H., et al., "Missing Value Estimation for DNA Microarray Gene Expression Data: Local Least Squares Imputation," Bioinformatics, vol. 21, No. 2, pp. 187-198, Oxford University Press, 2005.
Bar-Joseph, Z., Gerber, G., Lee, T., Rinaldi, N., Yoo, J., Robert, F., Gordon, D., Fraenkel, E., Jaahhola, T., Young, R., Gifford, D.: "Computational discovery of gene modules and regulatory networks, Nat. Biotechnol", 21 (2003) 1337-1342.
Boulesteix, A., Strimmer, K.: "Predicting transcription factor activities from combined analysis of microarray and ChIP data: a partial least squares approach", Theoretical Biology and Medical Modelling, (2005) 2:23.

Bozdağ, D., Parvin, J. D., Catalyurek, U. V.: "A biclustering method to discover co-regulated genes using diverse gene expression datasets", Lecture Notes in Bioinformatics 5462 (2009) 151-163.
Yu, H., Gerstein, M.: "Genomic analysis of the hierarchical structure of regulatory networks". Proceedings of National Academy of Sciences USA 103 (2006) 14724-14731.
Zeitlinger, J., Simon, I., Harbison, C., Hannett, N., Volkert, T., Fink, G., Young, R.: "Program-specific distribution of a transcription factor dependent on partner transcription factor and MAPK signaling". Cell, 113 (2003) 395-404.
Cho, R. J., Campbell, M. J., Winzeler, L. A., Steinmetz, L., Conway, A., Wodicka, L., Wolfsberg, T. G., Gabrielian, A. E., Landsman, D., Lockhart, D. J., Davis, R. W.: "A genome-wide transcriptional analysis of the mitotic cell cycle". Molecular Cell, 2 (1998) 65-73.
Das, R., Mitra, S., Banka, H. and Mukhopadhyay, S.: Evolutionary biclustering with correlation for gene interaction networks, Pattern Recognition and Machine Intelligence, Springer Verlag, LNCS 4815 (2007) 416-424.
Das, R., Mitra, S., Murthy, C.A., Mukhopadhyay, S.: "A Least Squares Fitting-Based Modeling of Gene Regulatory Sub-networks", (2009) S. Chaudhury et al. (Eds.) PReMI 2009, LNCS 5909, pp. 165-170.
Filkov, V., Skiena, S., Zhi, J.: "Analysis techniques for micro array time-series data". Journal of Computational Biology, 9 (2002) 317-330.
Kim, J., Bates, D., Postlethwaite, I., Heslop-Harrison, P., Cho, K.: "Least-squares methods for identifying biochemical regulatory networks from noisy measurements", BMC Bioinformatics, (2007) 8:8 (15 pages).
Mitra, S., Das, R., Banka, H. and Mukhopadhyay, S.: "Gene interaction—An evolutionary biclustering approach. Information Fusion", 10 (2009) 242-249.
Schmidt, H., Cho, K., Jacobsen, E.: "Identification of small scale biochemical networks based on general type system perturbations", FEBS Journal, (2005) 272:2141-2151.
Schmitt (Jr.), W., Raab, R., Stephanopoulos, G.: "Elucidation of gene interaction networks through time-lagged correlation analysis of transcriptional data", Genome Research, 14 (2006) 1654-1663.
Segal, E., Shapira, M., Regev, A., Pe'Er, D., Botstein, D., Koller, D. and Friedman, N.: "Module networks: Identifying regulatory modules and their condition-specific regulators from gene expression data". Nature Genetics, 34 (2003) 166-176.
Tagkopoulos, I., Slavov, N., Kung, S. Y.: "Multi-class biclustering and classification based on modeling of gene regulatory networks", Proceedings of the Fifth IEEE Symposium on Bioinformatics and Bioengineering, (2005) 89-96.

*Primary Examiner* — Jason Sims

(74) *Attorney, Agent, or Firm* — Foley & Lardner LLP

(57) ABSTRACT

Disclosed are methods and custom computing apparatuses for identifying gene-gene interactions from gene expression data, based on which a gene regulatory sub-network can be built. In particular, relationships in which multiple genes co-regulate one target gene can also be identified.

9 Claims, 2 Drawing Sheets

EXTRACTING GENE-GENE INTERACTIONS FROM GENE EXPRESSION DATA

TECHNICAL FIELD

This disclosure relates generally to methods and computing apparatuses pertaining to identifying gene-gene interactions and generating gene regulatory networks from gene expression data.

BACKGROUND

The following description is provided to assist the understanding of the reader. None of the information provided or references cited is admitted to be prior art.

Rapid development in DNA microarray technology has resulted in the parallel generation of expression data of thousands of genes of multiple organisms under various experimental conditions and/or time points. These gene expression data are prone to noise and ambiguity and may be unequally sampled over time. On the other hand, time series or multiple condition gene expression data are often under-determined, involving high-dimensional genes with very few time-points or conditions. An apparent similarity of expression profiles between a pair of genes may actually denote an indirect co-regulation by other genes, or may be due to a mere coincidence involving no causal relationship.

A gene regulatory network is comprised of genes interacting with each other, and acting as a complex input-output system for controlling cellular functions. It represents a complex structure consisting of various gene products activating or repressing other gene products. Transcription factor (TF) is a protein that interacts directly with its target gene(s) (T) by up regulating or down regulating its gene expression, thereby resulting in activation or inhibition of the target gene(s). A gene regulatory sub-network, by contrast, is a portion of a gene regulatory network. Understanding of a gene regulatory network, which demonstrates TF-T relationship, is helpful in elucidating basic biochemical mechanisms. Its impact on fast and accurate generation of gene regulatory pathways and associated gene regulatory sub-networks, for specific organs or tissues, is evident. Such information can then be used for understanding of a disease mechanism and used for drug design.

Identification of interactions between genes based on gene expression is a complex process involving delineation of linear as well as non-linear and higher-order interactions. Commonly used similarity measures, such as correlation analysis, do not consider non-linear or higher-order effects between genes.

SUMMARY

In one aspect, the present disclosure provides a method for generating a gene regulatory sub-network using a custom computing apparatus comprising at least one processor and a memory, the method comprising:

receiving, in the memory, gene expression data of a plurality of genes measured at two or more time points or conditions;

accessing, by the at least one processor, the gene expression data; and by the at least one processor, selecting a bicluster of genes and time points or conditions by performing a biclustering on the gene expression data, wherein the bicluster of genes and time points or conditions constitutes a subset of the gene expression data;

for each gene in the bicluster, calculating a sum of squares of error for fitting the gene to each of the remaining genes in the bicluster, thereby generating a plurality of sums of squares of error comprising a sum of squares of error for fitting every gene to every other gene in the bicluster, wherein a sum of squares of error is determined by Equation (I):

$$S_{12}^2 \equiv \frac{1}{n}\left[\sum_{i=1}^{n}\{e_{2i} - E_{2i}(e_{1i})\}^2\right] \quad (I)$$

wherein:

$S_{12}^2$ denotes the sum of squares of error for fitting a gene (1) to a gene (2);

n denotes the number of time points or conditions in the bicluster;

$e_{1i}$ denotes the expression of gene (1) at the ith time point or condition;

$e_{2i}$ denotes the expression of gene (2) at the ith time point or condition; and $E_{2i}(e_{1i})$ denotes the estimate of $e_{2i}$ based on $e_{1i}$ at the ith time point or condition and is determined by Equation (II):

$$E_{2i}(e_{1i}) = \alpha_0 + \alpha_1 e_{1i} + \alpha_2 e_{1i}^2 + \ldots + \alpha_k e_{1i}^k \quad (II)$$

wherein:

k is a positive integer; and $\alpha_0$-$\alpha_k$ each denotes the coefficient of the kth order fitted polynomial and is determined by solving:

$$\frac{\partial S_{12}^2}{\partial a_j} = 0; \quad j = 0, 1, \ldots, k; \quad (III)$$

determining a cutoff value from the plurality of sums of squares of error, wherein a sum of squares of error for fitting a first gene to a second gene less than the cutoff value identifies a likely regulatory interaction from the first gene to the second gene; and building a gene regulatory sub-network with two or more genes in the bicluster, wherein each of the two or more genes has an identified likely regulatory interaction with at least one other gene of the two or more genes.

In another aspect, the present disclosure provides a custom computing apparatus comprising:

at least one processor;

a memory coupled to the at least one processor;

a storage medium in communication with the memory and the at least one processor, the storage medium containing a set of processor executable instructions that, when executed by the processor configure the custom computing apparatus to generate a gene regulatory sub-network, comprising a configuration to:

receive, in the memory, gene expression data of a plurality of genes measured at two or more time points or conditions;

access, by the at least one processor, the gene expression data; and by the at least one processor, selecting a bicluster of genes and time points or conditions by performing a biclustering on the gene expression data, wherein the bicluster of genes and time points or conditions constitutes a subset of the gene expression data;

for each gene in the bicluster, calculating a sum of squares of error for fitting the gene to each of the remaining genes in the bicluster, thereby generating a plurality of sums of squares of error comprising a sum of squares of error for fitting every gene to every other gene in the bicluster, wherein a sum of squares of error is determined by Equation (I):

$$S_{12}^2 \equiv \frac{1}{n}\left[\sum_{i=1}^{n}\{e_{2i} - E_{2i}(e_{1i})\}^2\right] \quad (I)$$

wherein:

$S_{12}^2$ denotes the sum of squares of error for fitting a gene (1) to a gene (2);

n denotes the number of time points or conditions in the bicluster;

$e_{1i}$ denotes the expression of gene (1) at the ith time point or condition;

$e_{2i}$ denotes the expression of gene (2) at the ith time point or condition; and $E_{2i}(e_{1i})$ denotes the estimate of $e_{2i}$ based on $e_{1i}$ at the ith time point or condition and is determined by Equation (II):

$$E_{2i}(e_{1i}) \equiv \alpha_0 + \alpha_1 e_{1i} + \alpha_2 e_{1i}^2 + \ldots + \alpha_k e_{1i}^k \quad (II)$$

wherein:

k is a positive integer; and $\alpha_0$-$\alpha_k$ each denotes the coefficient of the kth order fitted polynomial and is determined by solving:

$$\frac{\partial S_{12}^2}{\partial a_j} = 0; \quad j = 0, 1, \ldots, k; \quad (III)$$

determining a cutoff value from the plurality of sums of squares of error, wherein a sum of squares of error for fitting a first gene to a second gene less than the cutoff value identifies a likely regulatory interaction from the first gene to the second gene; and building a gene regulatory sub-network with two or more genes in the bicluster, wherein each of the two or more genes has an identified likely regulatory interaction with at least one other gene of the two or more genes.

In some embodiments of the above method or computing apparatus, when a likely regulatory interaction is identified both from a first gene to a second gene and from the second gene to the first gene, the sum of squares of error for fitting the first gene to the second less than the sum of squares of error for fitting the second gene to the first gene identifies that the first gene likely affects the second gene more than the second gene affects the first gene. In some embodiments, the cutoff value is determined as the thirty third percentile of the plurality of sums of squares of error. In some embodiments, k is 3.

In another embodiment, the disclosure provides a method for identifying a multiple-gene to one gene regulatory set wherein the multiple genes likely co-regulate the one gene using a custom computing apparatus comprising at least one processor and a memory, the method comprising:

receiving, in the memory, gene expression data of a plurality of genes measured at two or more time points or conditions;

accessing, by the at least one processor the gene expression data; and by the at least one processor, for each gene of the plurality of genes, calculating a sum of squares of error for fitting every multiple-gene combination selected from the remainder of the plurality of genes to the gene, thereby generating a plurality of sums of squares of error for all multiple-gene to one gene sets from the plurality of genes;

determining a cutoff value from the plurality of sums of squares of error, wherein a sum of squares of error for fitting a multiple-gene combination to a one gene less than the cutoff value identifies the genes of the multiple-gene combination as likely co-regulating the one gene, thereby identifying a multiple-gene to one gene regulatory set.

In another embodiment, the disclosure provides a custom computing apparatus comprising:

at least one processor;

a memory coupled to the at least one processor;

a storage medium in communication with the memory and the at least one processor, the storage medium containing a set of processor executable instructions that, when executed by the processor configure the custom computing apparatus to identify a multiple-gene to one gene regulatory set wherein the multiple genes likely co-regulate the one gene, comprising a configuration to:

receive, in the memory, gene expression data of a plurality of genes measured at two or more time points or conditions;

access, by the at least one processor the gene expression data; and by the at least one processor, for each gene of the plurality of genes, calculating a sum of squares of error for fitting every multiple-gene combination selected from the remainder of the plurality of genes to the gene, thereby generating a plurality of sums of squares of error for all multiple-gene to one gene sets from the plurality of genes;

determining a cutoff value from the plurality of sums of squares of error, wherein a sum of squares of error for fitting a multiple-gene combination to a one gene less than the cutoff value identifies the genes of the multiple-gene combination as likely co-regulating the one gene, thereby identifying a multiple-gene to one gene regulatory set.

In one embodiment, the sum of squares of error for fitting a multiple-gene combination to a one gene is determined by Equation (IV):

$$S^2 \equiv \frac{1}{n}\left[\sum_{i=1}^{n}\{e_{1i} - E_{1i}\}^2\right] \quad (IV)$$

wherein:

$S^2$ denotes the sum of squares of error for fitting the multiple-gene combination to the one gene;

n denotes the number of time points or conditions;

$e_{1i}$ denotes the expression of the one gene at the ith time point; and $E_{1i}$ denotes the estimate of $e_{1i}$ based on the expression of the genes of the multiple-gene combination. In some embodiments, $E_{1i}$ is determined by a polynomial. In a particular embodiment, the polynomial is a second order polynomial.

$E_{1i}$, in one aspect, can be determined by Equation (V):

$$E_{1i} = \alpha_0 + \sum_{j=1}^{m} \alpha_j * e_{ji} + \sum_{\forall j,k=1}^{m} \alpha_{jk} * e_{ji} * e_{ki} \qquad \text{(V)}$$

wherein:
m denotes the number of genes in a multi-gene combination;
$e_{ji}$ each denotes one gene of the multiple-gene combination;
$e_{ki}$ each denotes one gene of the multiple-gene combination; and
$\alpha_0$ and each of $\alpha_j$ and $\alpha_{jk}$ each denotes a coefficient of the polynomial and the coefficients are obtained by solving the corresponding normal Equations of $\alpha_0$, $\alpha_j$ and $\alpha_{jk}$ (VI):

$$\frac{\partial S^2}{\partial \alpha_0} = 0; \quad \frac{\partial S^2}{\partial \alpha_j} = 0; \quad \text{or} \quad \frac{\partial S^2}{\partial \alpha_{jk}} = 0;. \qquad \text{(VI)}$$

In another aspect, the multi-gene combination is a two-gene combination and $E_{1i}$ is determined by Equation (VII):

$$E_{1i} = \alpha_0 + \alpha_1 * e_{1i} + \alpha_2 * e_{2i} + \alpha_3 * e_{1i}^2 + \alpha_4 * (e_{1i} * e_{2i}) + \alpha_5 * e_{2i}^2 \qquad \text{(VII)}$$

wherein:
$e_{1i}$ and $e_{2i}$ each denotes one gene of the two-gene combination potentially affecting the one gene; and
$\alpha_0$-$\alpha_5$ each denotes a coefficient of the polynomial and the coefficients are obtained by solving the corresponding normal Equations of $\alpha_0$-$\alpha_5$ (VIII):

$$\frac{\partial S^2}{\partial \alpha_j} = 0; \quad j = 0, 1, \ldots, 5. \qquad \text{(VIII)}$$

A cutoff, in some embodiments, is determined as the thirty third percentile of the plurality of sums of squares of errors, or alternatively as the twenty fifth percentile of the plurality of sums of squares of errors.

In some embodiments, the gene expression data of the above methods or computing apparatuses is selected as a bicluster from a larger gene expression data set by performing a biclustering on the larger gene expression data, wherein the larger gene expression data set further includes expression data from genes not found in the bicluster, or expression data measured at time points or conditions not found in the bicluster, or both.

For any of the foregoing methods or steps carried by any of the foregoing computing apparatuses, the gene regulatory sub-network or multiple-gene to one gene regulatory set can be validated with gene ontology study or an experiment. These gene regulatory sub-networks or multiple-gene to one gene regulatory sets, in another aspect, can be displayed on a screen in a suitable format.

The foregoing summary is illustrative only and is not intended to be in any way limiting. In addition to the illustrative aspects, embodiments, and features described above, further aspects, embodiments, and features will become apparent by reference to the following drawings and the detailed description.

DETAILED DESCRIPTION

Figure 1:
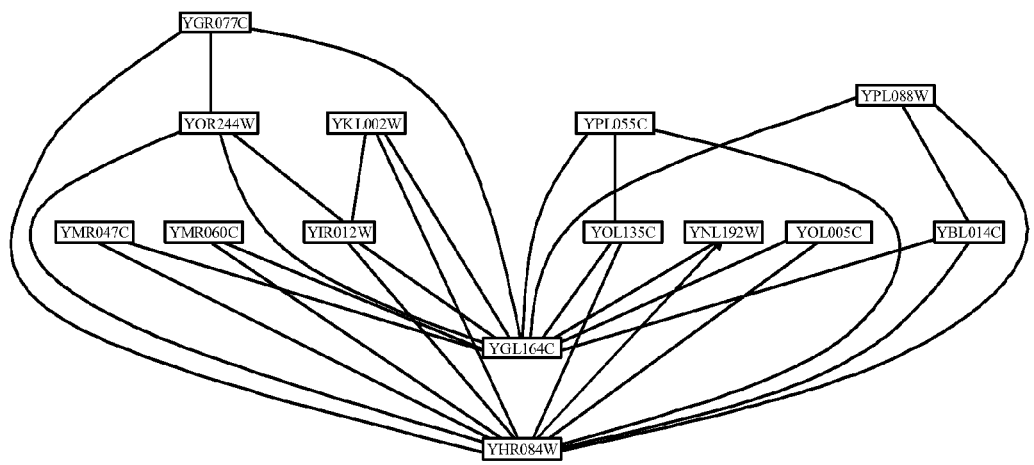
FIG. 1 illustrates an illustrative gene regulatory sub-network derived from a bicluster of 14 genes showing a regulatory interaction from transcription factor YHR084W to target gene YNL192W, as indicated by the arrow.

In the following detailed description, reference may be made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present technology is described herein using, unless otherwise stated, the singular forms "a," "an," and "the" include plural reference. Thus, for example, a reference to "a gene" includes a plurality of genes, and a reference to "a transcription factor" is a reference to one or more transcription factors.

The present disclosure provides for efficient and automated extraction of complex interactions and reconstruction of gene regulatory sub-networks from gene expression data.

Unlike correlation-based similarity measures such as Pearson correlation coefficient or Spearman's rank correlation coefficient, which do not consider non-linear effects among genes, the present technology takes advantage of least squares fitting and thus takes into account higher-order dependencies between gene pairs. Additionally, by penalizing models based on the number of parameters, the present technology prevents over-fitting.

The Pearson correlation coefficient and Spearman's rank correlation coefficient have been used to identify interactions between genes based on gene expression data. The microarray technology, being sensitive to intrinsic noise, poses challenges to the simple correlation based approaches because a correlation may be observed between genes of regulatory relationship. For example, Filkov et al. have shown that less than 20% of the known regulatory gene pairs exhibit strong correlations (Filkov et al. (2002) *J. Comp. Bio.* 9:317-30). Therefore, simple correlation has inherent difficulties, and it can only serve as a satisfactory measure of relationship between a pair of genes when the two are linearly related. The novel use of the least squares fitting method in this disclosure, by contrast, also takes care of most non-linear and higher-order dependencies between gene pairs.

By way of illustration, from a bicluster of 1173 genes which includes 357 interactions as evidenced by genetic, biochemical and ChIP-chip biological experiments in yeast (Yu and Gerstein (2006) *Proc. Nat. Acad. Sci. USA* 103: 14724-31), the correlation-based methods could retrieve only 287 and 307 of these interactions, using the Pearson (Mitra et al. (2009) *Information Fusion* 10:242-9)) and Spearman's (Das et al. (2007) *Springer Verlag, LNCS* 4815:416-24) coefficient methods respectively, after elimination of the weakly correlated gene pairs. With the methods of the present disclosure, 332 of these biologically validated relations were identified.

Thus, one aspect of the present disclosure provides a method for generating a gene regulatory sub-network using a custom computing apparatus including at least one processor and a memory. The method includes receiving, in the memory, gene expression data of a plurality of genes measured at two or more time points or conditions and accessing, by the at least one processor, the gene expression data. In one aspect, biclustering can be used, as a preprocessing step, to extract a subset of conditions or time points under which a subset of genes are co-expressed or co-regulated from a set of gene expression data, thereby reducing the search space and associated computational complexity.

A "gene regulatory sub-network" or "gene sub-network" refers to a collection of two or more genes, each of which is connected to another either directly or indirectly through one or more other genes in the collection. A "connection" between two genes connotes a regulatory interaction between the genes. For the purpose of illustration only, FIG. 1 shows a gene regulatory sub-network identified in Example 1. Each edge in the figure indicates a possible interaction between two genes, such as between YGR077C and YGL164C, which may be directly related. This is expected to be significant enough for further consideration in wet lab analysis. Genes in a network that do not have an edge between them may be indirectly related. For example, YGR077C may be indirectly connected to YPL088W through YHR084W.

The biclustering process is useful in elimination of redundant genes leading to extraction of biologically more meaningful partitions of gene expression data. Methods of performing biclustering on a gene expression dataset are generally known in the art. For example, Mitra et al. ((2009) *Information Fusion* 10:242-9) and Das et al. ((2007) *Springer Verlag, LNCS* 4815:416-24) disclose the generation of biclusters using multi-objective evolutionary optimization methods.

In another aspect, pairwise sums of squares of error (SSE) are calculated by the processor for fitting each of the genes in the bicluster to each of remaining genes in the bicluster, thereby generating a list of SSE's. In one embodiment, the SSE is determined by Equation (I):

$$S_{12}^2 \equiv \frac{1}{n}\left[\sum_{i=1}^{n}\{e_{2i} - E_{2i}(e_{1i})\}^2\right] \quad (I)$$

wherein:
$S_{12}^2$ denotes the sum of squares of error for fitting a gene (1) to a gene (2);
n denotes the number of time points or conditions in the bicluster;
$e_{1i}$ denotes the expression of gene (1) at the ith time point or condition;
$e_{2i}$ denotes the expression of gene (2) at the ith time point or condition; and
$E_{2i}(e_{1i})$ denotes the estimate of $e_{2i}$ based on $e_{1i}$ at the ith time point or condition.

In one embodiment, $E_{2i}(e_{1i})$ is determined by Equation (II):

$$E_{2i}(e_{1i}) \equiv \alpha_0 + \alpha_1 e_{1i} + \alpha_2 e_{1i}^2 + \ldots + \alpha_k e_{1i}^k \quad (II)$$

wherein:
k is a positive integer; and
$\alpha_0$-$\alpha_k$ each denotes the coefficient of the kth order fitted polynomial and is determined by solving:

$$\frac{\partial S_{12}^2}{\partial a_j} = 0; \quad j = 0, 1, \ldots, k. \quad (III)$$

Alternatively, in some embodiments, let e represent a gene's expression profile over a series of n time points or conditions, and let $S_{12}^2$ denote the residual or the sum of squares of the error of estimation for fitting gene $e_1$ to $e_2$ (sampled at $e_{1i}$ and $e_{2i}$ over n time intervals). $S_{12}^2$ can be determined by:

$$S_{12}^2 \equiv \frac{1}{n}\left[\sum_{i}\{e_{2i} - (a_0 + a_1 e_{1i} + a_2 e_{1i}^2 + \ldots + a_k e_{1i}^k)\}^2\right],$$

wherein $\alpha_j$'s (j=0, 1, . . . , k) denote the (k+1) coefficients of the kth order fitted polynomial, and $\alpha_0 + \alpha_1 e_{1i} + \alpha_2 e_{1i}^2 + \ldots + \alpha_k e_{1i}^k$ generates an estimate ($E_{2i}$) of $e_2$ for a given or observed $e_1$.

Similarly, the residual or the sum of squares of error for fitting $e_2$ to $e_1$ can be represented as $$S_{21}^2 \equiv \frac{1}{n}\left[\sum_{i}\{e_{1i} - (b_0 + b_1 e_{2i} + b_2 e_{2i}^2 + \ldots + b_k e_{2i}^k)\}^2\right],$$

wherein $b_j$'s (j=0, 1, . . . , k) correspond to the (k+1) coefficients in this kth order fitted polynomial.

In one embodiment, k is 1, or alternatively 2, or 3, or 4, or 5, or 6, or 7, or 8, or 9, or 10 . . . (n−1), wherein n denotes the number of time points or conditions in the bicluster. In another embodiment, k is 2 or 3.

The coefficients, $\alpha_j$'s and $b_j$'s, can be obtained by solving their corresponding (k+1) normal equations:

$$\frac{\partial S_{12}^2}{\partial a_j} = 0; \quad j = 0, 1, \ldots, k \text{ or}$$

$$\frac{\partial S_{21}^2}{\partial b_j} = 0; \quad j = 0, 1, \ldots, k.$$

The errors can be represented as $\xi_1 = \xi(e_1, e_2) = \sqrt{S_{12}^2}$ or $\xi_2 = \xi(e_2, e_1) = \sqrt{S_{21}^2}$.

The minimum error between a gene x and a gene y is selected as:
$\xi_1$ if $\xi(x,y) \langle \xi(y,x)$ or
$\xi_2$ otherwise.

It is further noted that, in some embodiments, between a gene x and a gene y, $\xi(x,y) \langle (y,x)$ indicates that gene x affects gene y more than gene y affects gene x. $\xi(y,x) \langle (x,y)$, on the other hand, indicates that gene y affects gene x more than gene x affects gene y.

In one embodiment, an error matrix, Err(i, j) with $1 \leq i, j \leq N$ and N being the total number of genes present in the selected bicluster, is created. Since the bicluster constitutes a smaller space than the entire gene expression data set generated, for example, by a microarray, the computational requirement is naturally diminished and leads to faster convergence.

The error matrix, in another embodiment, is then discretized for eliminating larger errors which contribute less towards regulation. In this context, the error range is divided into partitions and a cutoff value is determined from the partitions. In one embodiment, the partitions are two partitions divided by a median. In another embodiment, the partitions are tertile, or alternatively quartile, quintile, nonile, decile, duo-decile, vigintile, percentile or yet alternatively permillage partitions. In one embodiment, the cutoff value, Q, is the median of the errors in the error range, or alternatively, either of the tertiles, any of the quantiles, any of the quintiles, noniles, deciles, duo-deciles, vigintiles, percentiles or yet alternatively any of the permillages of the error range. Accordingly, in some embodiments, the cutoff value Q is the 1st percentile, or alternatively the 2nd, the 5th, the 10th, the 15th, the 20th, the 25th, the 33rd, the 40th, the 45th, the 50th, the 66th, the 75th, the 80th, or the 90th percentile of the error range.

In yet another embodiment, the cutoff value Q can be determined based on the distribution of the error values. A non-limiting example of a cutoff value Q can be the mean of errors (m) minus the standard deviation (σ) in the error range: m±σ, or alternatively m±k×σ wherein k is a positive number, such as, but not limited to 0.1, 0.25, 0.5, 1, 1.5, 2 or 2.5.

In some embodiments, accordingly, the criteria for selecting a cutoff value Q are pre-determined, as illustrated above, eliminating the need for user-defined parameters.

The error matrix can be discretized according to the cutoff value Q by an adjacent matrix A(i,j). In one aspect, A(i, j)=1 when Err(i,j)≦Q so that Err(i, j) is retained while transformed by the adjacency matrix. These indicate likely interactions between genes. In another aspect, A(i, j)=0 when Err(i,j)>Q to remove background noise. In some embodiments of the present disclosure, an error for fitting a gene to itself is not calculated, assuming absence of self interaction.

Thereafter, a gene regulatory sub-network connecting the genes having interactions shown as having A(i, j)=1, is generated. Methods of building a gene regulatory sub-network with identified gene interactions are generally known in the art, and various computer programs are available for free or commercially for generating a visual display of gene regulatory sub-networks. In one aspect, the matrix A(i,j) on its own represents a gene regulatory sub-network, with a value 1 for A(i,j) indicating an interaction from gene i to gene j, and a value 0 indicating a lack of interaction from gene i to j. In another embodiment, a figure like FIG. 1, including nodes and edges, can be used to visually display a gene regulatory sub-network, with a node indicating a gene and an edge indicating an interaction. The visual representations, in some embodiments, can be displayed on a screen, or a printing platform, in a suitable format.

Yet in some embodiments, a gene regulatory sub-network generated with the methods of computing apparatuses can be validated by gene ontology study or an experiment. A public gene ontology database is available at the web address www-.geneontology.org.

The present disclosure further provides methods and custom computing apparatus for identifying multiple-gene to one gene regulatory sets from gene expression data. In a multiple-gene to one gene regulatory set, one target gene (T) is co-regulated by two or more genes that code for gene products, such as proteins or RNA, that regulate the target gene. In one aspect, the gene product that regulates a target gene is a transcription factor (TF). Alternatively, the interactions that exist between a target gene and a gene of the one or more genes that regulate the target gene may include, without limitation, miRNA (micro RNA)-RNA interaction, protein-DNA binding site interaction, protein-protein interaction, and additional biological interactions as defined in gene ontology (GO).

A "multiple-gene to one gene regulatory set" as used herein refers to a collection of three or more genes one of which, the "one gene", is co-regulated by the remaining two or more genes, the "multiple genes". Similarly, a "two-gene to one gene regulatory set" refers to a collection of three genes one of which, the "one gene", is co-regulated by the other "two genes".

The gene expression data of the above methods or computing apparatuses, in one embodiment, is selected as a bicluster from a larger gene expression data set by performing a biclustering on the larger gene expression data, wherein the larger gene expression data set further includes expression data from genes not found in the bicluster, or expression data measured at time points or conditions not found in the bicluster, or both.

The gene expression data of the above methods or computing apparatuses, in another embodiment, have been analyzed to generate a gene regulatory sub-network by other methods known in the art or otherwise disclosed in the present disclosure, and the multiple-gene to one gene regulatory sets identified herein can, therefore, further supplement a gene regulatory sub-network by more fully showing the co-regulation of a target gene by multiple other genes.

Accordingly, in one embodiment, the disclosure provides a method for identifying a multiple-gene to one gene regulatory set wherein the multiple genes likely co-regulate the one gene using a custom computing apparatus including at least one processor and a memory, the method including:

receiving, in the memory, gene expression data of a plurality of genes measured at two or more time points or conditions;

accessing, by the at least one processor the gene expression data; and by the at least one processor, for each gene of the plurality of genes, calculating a sum of squares of error for fitting every multiple-gene combination selected from the remainder of the plurality of genes to the gene, thereby generating a plurality of sums of squares of error for all multiple-gene to one gene sets from the plurality of genes;

determining a cutoff value from the plurality of sums of squares of error, wherein a sum of squares of error for fitting a multiple-gene combination to a one gene less than the cutoff value identifies the genes of the multiple-gene combination as likely co-regulating the one gene, thereby identifying a multiple-gene to one gene regulatory set.

In one embodiment, the sum of squares of error for fitting a multiple-gene combination to a one gene is determined by Equation (IV):

$$S^2 = \frac{1}{n}\left[\sum_{i=1}^{n}\{e_{1i} - E_{1i}\}^2\right] \quad (IV)$$

wherein:

$S^2$ denotes the sum of squares of error for fitting the multiple-gene combination to the one gene;

n denotes the number of time points or conditions;

$e_{1i}$ denotes the expression of the one gene at the ith time point; and $E_{1i}$ denotes the estimate of $e_{1i}$ based on the expression of the genes of the multiple-gene combination. In some embodiments, $E_{1i}$ is determined by a polynomial. In one embodiment, the polynomial is a second order polynomial.

$E_{1i}$, in one embodiment, can be determined by Equation (V):

$$E_{1i} = \alpha_0 + \sum_{j=1}^{m}\alpha_j * e_{ji} + \sum_{\forall j,k=1}^{m}\alpha_{jk} * e_{ji} * e_{ki} \quad (V)$$

wherein:

m denotes the number of genes in a multi-gene combination;

$e_{ji}$ each denotes one gene of the multiple-gene combination;

$e_{ki}$ each denotes one gene of the multiple-gene combination; and $\alpha_0$ and each of $\alpha_j$ and $\alpha_{jk}$ each denotes a coefficient of the polynomial and the coefficients are obtained by solving the corresponding normal Equations of $\alpha_0$, $\alpha_j$ and $\alpha_{jk}$ (VI):

$$\frac{\partial S^2}{\partial \alpha_0} = 0; \frac{\partial S^2}{\partial \alpha_j} = 0; \text{ or } \frac{\partial S^2}{\partial \alpha_{jk}} = 0; . \tag{VI}$$

In one embodiment, the genes in the multi-gene combination code for transcription factors (TFs). Alternatively, the interactions that exist between a target gene and a gene of the one or more genes that regulate the target gene may include, without limitation, miRNA (micro RNA)-RNA interaction, protein-DNA binding site interaction, protein-protein interaction, and additional biological interactions as defined in gene ontology (GO).

In another embodiment, the multi-gene combination is a two-gene combination and $E_{1i}$ is determined by Equation (VII):

$$E_{1i} = \alpha_0 + \alpha_1 * e_{1i} + \alpha_2 * e_{2i} + \alpha_3 * e_{1i}^2 + \alpha_4 * (e_{1i} * e_{2i}) + \alpha_5 * e_{2i}^2 \tag{VII}$$

wherein:

$e_{1i}$ and $e_{2i}$ each denotes one gene of the two-gene combination potentially affecting the one gene; and $\alpha_0$-$\alpha_5$ each denotes a coefficient of the polynomial and the coefficients are obtained by solving the corresponding normal Equations of $\alpha_0$-$\alpha_5$ (VIII):

$$\frac{\partial S^2}{\partial \alpha_j} = 0; j = 0, 1, \ldots, 5. \tag{VIII}$$

An error matrix can then be populated with errors calculated from any embodiments of the above methods. For example, for a two-gene to one-gene regulatory set, an error matrix having $\xi(i; j, k)$ as entries can be used to represent errors generated for each combination. A finding of $\xi(i; j, k) < \xi(j; k, i)$ and $\xi(k; i, j)$ would indicate that genes j and k have more impact on gene i than genes k and i on gene j or genes i and j on gene k.

In one embodiment, the cutoff value is the median of the errors in the error range, or alternatively, either of the tertiles, any of the quantiles, any of the quintiles, noniles, deciles, duo-deciles, vigintiles, percentiles or yet alternatively any of the permillages of the error range. Accordingly, in one embodiment, the cutoff value is the 1st percentile, or alternatively the 2nd, the 5th, the 10th, the 15th, the 20th, the 25th, the 33rd, the 40th, the 45th, the 50th, the 66th, the 75th, the 80th, or the 90th percentile of the error range.

In yet another embodiment, the cutoff value can be determined based on the distribution of the error values. A non-limiting example of a cutoff value can be the mean of errors (m) minus the standard deviation ($\sigma$) in the error range: m±$\sigma$, or alternatively m±k×$\sigma$ wherein k is a positive number, such as, but not limited to 0.1, 0.25, 0.5, 1, 1.5, 2 or 2.5.

Once the cutoff value is determined, multiple-gene to one gene regulatory sets can be identified accordingly. In one embodiment, a sum of squares of error for fitting a multiple-gene combination to a one gene less than the cutoff value identifies the genes of the multiple-gene combination as likely co-regulating the one gene. This information, subsequently, can be used to build parts of a gene regulatory network, or to supplement an existing gene regulatory network.

Methods of building a gene regulatory sub-network with identified gene interactions are generally known in the art and have been further disclosed supra.

Yet, in some embodiments, a gene regulatory sub-network generated with the methods or the computing apparatuses can be validated by gene ontology study or an experiment. A public gene ontology database is available at the web address www.geneontology.org.

Computing Devices of the Present Technology

Figure 2:
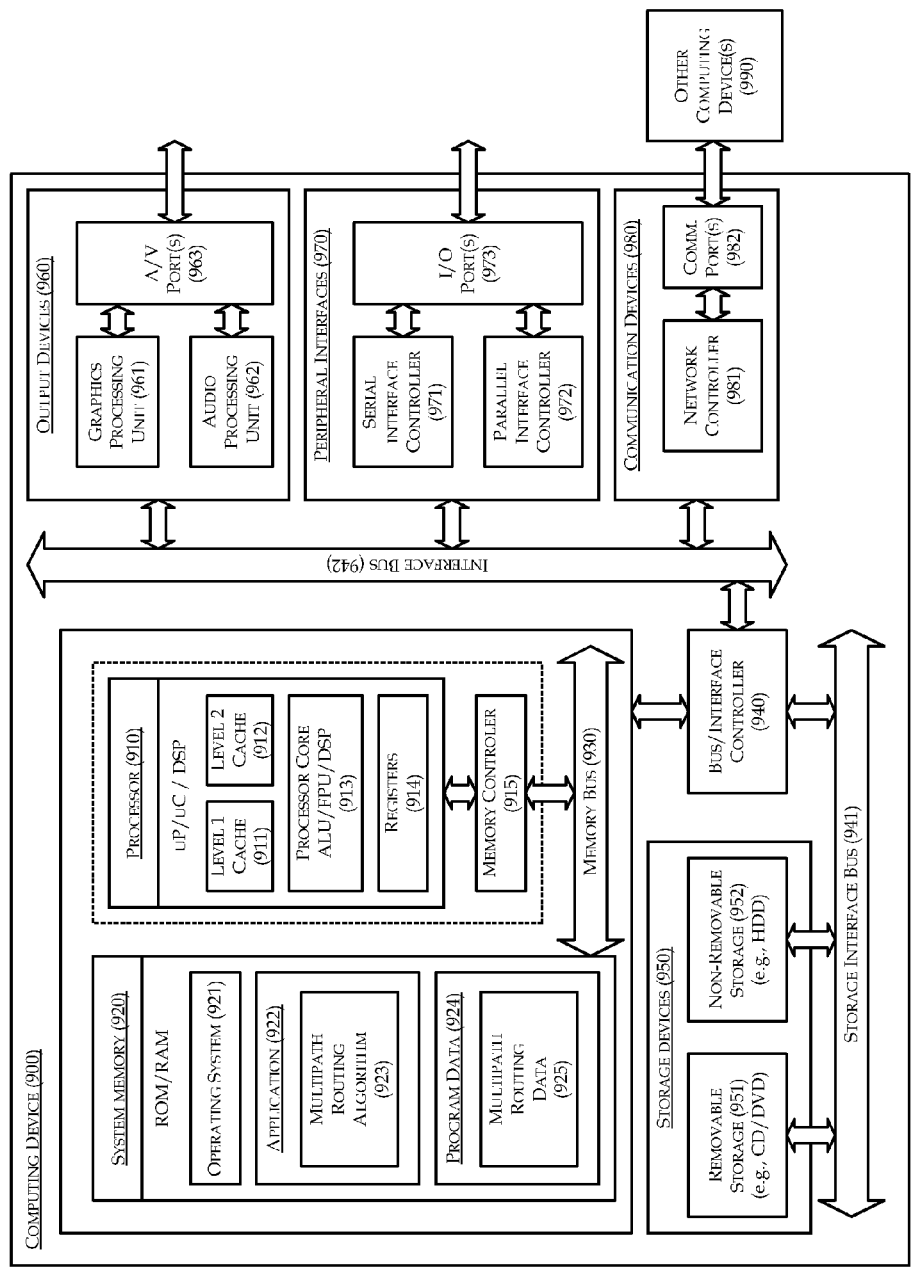
FIG. 2 shows an illustrative computing device suitable for use with the present disclosure.

FIG. 2 is a block diagram illustrating an example computing device 900 that is arranged for identifying gene-gene interactions or generating gene regulatory sub-networks from gene expression data in accordance with the present disclosure. In a very basic configuration 901, computing device 900 typically includes one or more processors 910 and system memory 920. A memory bus 930 may be used for communicating between the processor 910 and the system memory 920.

Depending on the desired configuration, processor 910 may be of any type including but not limited to a microprocessor (μP), a microcontroller (μC), a digital signal processor (DSP), or any combination thereof. Processor 910 may include one more levels of caching, such as a level one cache 911 and a level two cache 912, a processor core 913, and registers 914. An example processor core 913 may include an arithmetic logic unit (ALU), a floating point unit (FPU), a digital signal processing core (DSP Core), or any combination thereof. An example memory controller 915 may also be used with the processor 910, or in some implementations the memory controller 915 may be an internal part of the processor 910.

Depending on the desired configuration, the system memory 920 may be of any type including but not limited to volatile memory (such as RAM), non-volatile memory (such as ROM, flash memory, etc.) or any combination thereof. System memory 920 may include an operating system 921, one or more applications 922, and program data 924. Application 922 may include a least squares fitting method 923 that is arranged to identify gene-gene interactions or generate gene regulatory sub-networks from gene expression data. Program Data 924 may include gene expression data 925 that may be useful for identifying gene-gene interactions or generating gene regulatory sub-networks as will be further described below. In some embodiments, application 922 may be arranged to operate with program data 924 on an operating system 921 such that identification of gene-gene interactions or generation of gene regulatory sub-networks may be provided as described herein. This described basic configuration is illustrated in FIG. 2 by those components within dashed line 901.

Computing device 900 may have additional features or functionality, and additional interfaces to facilitate communications between the basic configuration 901 and any required devices and interfaces. For example, a bus/interface controller 940 may be used to facilitate communications between the basic configuration 901 and one or more data storage devices 950 via a storage interface bus 941. The data storage devices 950 may be removable storage devices 951, non-removable storage devices 952, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 920, removable storage 951 and non-removable storage 952 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 900. Any such computer storage media may be part of device 900.

Computing device 900 may also include an interface bus 942 for facilitating communication from various interface devices (e.g., output interfaces, peripheral interfaces, and communication interfaces) to the basic configuration 901 via the bus/interface controller 940. Example output devices 960 include a graphics processing unit 961 and an audio processing unit 962, which may be configured to communicate to various external devices such as a display or speakers via one or more A/V ports 963. Example peripheral interfaces 970 include a serial interface controller 971 or a parallel interface controller 972, which may be configured to communicate with external devices such as input devices (e.g., keyboard, mouse, pen, voice input device, touch input device, etc.) or other peripheral devices (e.g., printer, scanner, etc.) via one or more I/O ports 973. An example communication device 980 includes a network controller 981, which may be arranged to facilitate communications with one or more other computing devices 990 over a network communication link via one or more communication ports 982.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 900 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 900 may also be implemented as a personal computer including both laptop computer and non-laptop computer configurations.

EXAMPLES

The methods and computing apparatuses of the present disclosure will be understood more readily by reference to the following examples, which are provided by way of illustration and are not intended to be limiting of the present methods and computing apparatuses.

Example 1

Generation of Gene Regulatory Sub-Networks with Yeast Gene Expression Data

In this example, a yeast cell-cycle CDC28 gene expression data set as disclosed in Cho et al. (1998) *Molecular Cell* 2:65-73, which includes expression of 6220 genes at 17 time points taken at intervals of 10-minutes generated on Affymetrix oligonucleotide arrays, was chosen to test the methods and apparatuses of the present disclosure.

First, genes that were not annotated and genes having more than 30% missing expression values were removed from the data set. A total of 6029 genes were taken for imputation of missing values. While computing the errors, the order of the polynomial, k, was chosen as 1 (linear), 2 (quadratic) or 3 (cubic). It was noticed that better fitting (lower error) was provided by a cubic polynomial fit. The stronger interactions between genes in a gene pair were retained for generating a sub-network between various genes.

A sample extracted sub-network, including a bicluster of 14 genes for k=3, is depicted in FIG. 1. A transcription factor is connected to its target gene by an arrow if such a transcription factor (TF)—target gene (T) pair existed within any of the biclusters. The biclusters were biologically validated from gene ontology study, based on the statistically significant GO annotation database available at db.yeastgenome.org/cgi-bin/GO/goTermFinder.

The interaction between the TF-T pair YHR084W-YNL192W, extracted by the present technology is indicated by the directed arrow in FIG. 1. The interaction is validated from literature (Yu and Gerstein (2006) *Proc. Nat. Acad. Sci. USA* 103:14724-31). The relationship may be due to mating-specific binding behavior or, may belong to an additional mechanism for cell fusion. This is further established from the Saccharomyces Genome Database (SGD) at www.yeastgenome.org.

Analogously, the interactions depicted by the remaining links are expected to be significant enough for further consideration in wet lab analysis. Interestingly, now the links requiring exploration are reasonably less in number as compared to an exhaustive analysis (as conventionally required by biologists). This, therefore, serves to ease the computational burden for the biologists, and can serve as a suitable assistance.

The methods of the present technology have not yet encountered any false positive or false negative finding on this dataset or other datasets tested.

Using the method of the present disclosure, the inventors were able to identify interactions that could not be identified by conventional methods, which suggests that additional non-linear interactions can be extracted. In summary, these data show that the methods of the present technology successfully extracted gene interactions from complex gene expression data.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 particles refers to groups having 1, 2, or 3 particles. Similarly, a group having 1-5 particles refers to groups having 1, 2, 3, 4, or 5 particles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All references cited herein are incorporated by reference in their entireties and for all purposes to the same extent as if each individual publication, patent, or patent application was specifically and individually incorporated by reference in its entirety for all purposes.

What is claimed is:

1. A method for generating a gene regulatory sub-network using a custom computing apparatus comprising at least one processor and a memory, the method comprising:
   receiving, in the memory, gene expression data of a plurality of genes measured at two or more time points or conditions;
   accessing, by the at least one processor, the gene expression data; and
   by the at least one processor,
      selecting a bicluster of genes and time points or conditions by performing a biclustering on the gene expression data, wherein the bicluster of genes and time points or conditions constitutes a subset of the gene expression data;
      for each gene in the bicluster, calculating a sum of squares of error for fitting the gene to each of the remaining genes in the bicluster, thereby generating a plurality of sums of squares of error comprising a sum of squares of error for fitting every gene to every other gene in the bicluster, wherein a sum of squares of error is determined by Equation (I):

$$S_{12}^2 \equiv \frac{1}{n}\left[\sum_{i=1}^{n} \{e_{2i} - E_{2i}(e_{1i})\}^2\right] \quad (I)$$

wherein:
   $S_{12}^2$ denotes the sum of squares of error for fitting a gene (1) to a gene (2);
   n denotes the number of time points or conditions in the bicluster;
   $e_{1i}$ denotes the expression of gene (1) at the ith time point or condition;
   $e_{2i}$ denotes the expression of gene (2) at the ith time point or condition; and
   $E_{2i}(e_{1i})$ denotes the estimate of $e_{2i}$ based on $e_{1i}$ at the ith time point or condition and is determined by Equation (II):

$$E_{2i}(e_{1i}) = \alpha_0 + \alpha_1 e_{1i} + \alpha_2 e_{1i}^2 + \ldots + \alpha_k e_{1i}^k \quad (II)$$

wherein:
   k is a positive integer; and
   $\alpha_0$-$\alpha_k$ each denotes the coefficient of the kth order fitted polynomial and is determined by solving:

$$\frac{\partial S_{12}^2}{\partial a_j} = 0; \, j = 0, 1, \ldots, k; \quad (III)$$

determining a cutoff value from the plurality of sums of squares of error, wherein a sum of squares of error for fitting a first gene to a second gene less than the cutoff value identifies a likely regulatory interaction from the first gene to the second gene; and
   building a gene regulatory sub-network with two or more genes in the bicluster, wherein each of the two or more genes has an identified likely regulatory interaction with at least one other gene of the two or more genes.

2. The method of claim 1, wherein when a likely regulatory interaction is identified both from a first gene to a second gene and from the second gene to the first gene, the sum of squares of error for fitting the first gene to the second less than the sum of squares of error for fitting the second gene to the first gene identifies that the first gene likely affects the second gene more than the second gene affects the first gene.

3. The method of claim 1, wherein the cutoff value is determined as the thirty third percentile of the plurality of sums of squares of error.

4. The method of claim 1, wherein k is 3.

5. The method of claim 1, wherein the cutoff value is determined as the twentieth percentile of the plurality of sums of squares of error.

6. The method of claim 1, wherein k is 2.

7. The method of claim 1, further comprising, prior to determining the cutoff value, creating an error matrix, Err(i, j)

with $1 \leq i, j \leq N$ and N being the total number of genes present in the selected bicluster, wherein each element in the error matrix is determined as $$\xi_{ij} = \sqrt{S_{ij}^2}.$$

8. The method of claim 7, wherein the cutoff value is determined from the error matrix.

9. The method of claim 8, further comprising discretizing the error matrix according to the cutoff value, wherein in the discretized matrix $A(i, j)$, $A(i,j)=1$ if $\text{Err}(i,j) \leq Q$, and $A(i,j)=0$ if $\text{Err}(i,j) > Q$, wherein Q denotes the cutoff value, and wherein the discretized matrix is used to build the gene regulatory subnetwork.

* * * * *

UNITED STATES PATENT AND TRADEMARK OFFICE
CERTIFICATE OF CORRECTION

PATENT NO. : 8,478,541 B2  
APPLICATION NO. : 12/854116  
DATED : July 2, 2013  
INVENTOR(S) : Mitra et al.

Page 1 of 1

It is certified that error appears in the above-identified patent and that said Letters Patent is hereby corrected as shown below:

On the Title Page, in Item (56), under "OTHER PUBLICATIONS", in Column 1, Line 17, delete "Biotechnol"," and insert -- Biotechnology", --, therefor.

In the Drawings:

In Fig. 2, Sheet 2 of 2, in Box "963", delete " A/V PORT(S) " and insert -- A/V PORT(S) --, therefor.

In Fig. 2, Sheet 2 of 2, in Box "910", in Line 1, delete "uP/uC/DSP" and insert -- µP/µC/DSP --, therefor.

In Fig. 2, Sheet 2 of 2, in Box "915", delete "MEMORY CONTROLER" and insert -- MEMORY CONTROLLER --, therefor.

Signed and Sealed this  
Twenty-sixth Day of November, 2013

Margaret A. Focarino  
*Commissioner for Patents of the United States Patent and Trademark Office*